(12) United States Patent
Ries et al.

(10) Patent No.: US 8,750,961 B1
(45) Date of Patent: Jun. 10, 2014

(54) IMPLANTABLE MEDICAL DEVICE HAVING A MULTI-AXIS MAGNETIC SENSOR

(71) Applicant: Medtronic, Inc., Minneapolis, MN (US)

(72) Inventors: Andrew J. Ries, Lino Lakes, MN (US); Mark E. Henschel, Phoenix, AZ (US); Lawrence C. McClure, Forest Lake, MN (US); Mark S. Ricotta, Tempe, AZ (US); Lejun Wang, San Diego, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/788,310

(22) Filed: Mar. 7, 2013

(51) Int. Cl.
*A61B 5/055* (2006.01)
*A61B 5/05* (2006.01)
*A61N 1/08* (2006.01)

(52) U.S. Cl.
USPC .............................. 600/407; 600/409; 607/52

(58) Field of Classification Search
None
See application file for complete search history.

(56) References Cited

U.S. PATENT DOCUMENTS

| | | | |
|---|---|---|---|
| 5,438,990 A | 8/1995 | Wahlstrand et al. | |
| 5,683,432 A | 11/1997 | Goedeke et al. | |
| 6,009,878 A | 1/2000 | Weijand et al. | |
| 6,738,670 B1 | 5/2004 | Almendinger et al. | |
| 7,187,978 B2 | 3/2007 | Malek et al. | |
| 7,301,332 B2 * | 11/2007 | Govari et al. | 324/207.21 |
| 7,313,430 B2 | 12/2007 | Urquhart et al. | |
| 7,525,309 B2 | 4/2009 | Sherman et al. | |
| 7,835,784 B2 | 11/2010 | Mire et al. | |
| 8,165,691 B2 | 4/2012 | Ellingson et al. | |
| 8,509,888 B2 * | 8/2013 | Linder et al. | 607/2 |
| 8,518,734 B2 * | 8/2013 | Whig et al. | 438/73 |
| 2004/0164840 A1 * | 8/2004 | Xiao et al. | 338/32 H |
| 2005/0027195 A1 | 2/2005 | Govari | |
| 2008/0299904 A1 * | 12/2008 | Yi et al. | 455/41.1 |
| 2010/0064536 A1 * | 3/2010 | Caskey et al. | 33/303 |

* cited by examiner

*Primary Examiner* — Brian T Gedeon
(74) *Attorney, Agent, or Firm* — Evans M. Mburu

(57) ABSTRACT

The present invention provides a packaging technique and apparatus that incorporates a flexible substrate package with a three-axis magnetic sensor for three-axis sensing in an implantable medical device. The apparatus includes three single-axis magnetic sensor integrated circuits (ICs) that are mounted to a substrate and encapsulated with a polymer mold compound. The substrate is excised around each of the sensor ICs to form panels that are folded to align the three single-axis sensors in the x, y and z axis.

20 Claims, 10 Drawing Sheets

IMPLANTABLE MEDICAL DEVICE HAVING A MULTI-AXIS MAGNETIC SENSOR

TECHNICAL FIELD

The present invention relates to medical systems and devices and more particularly to sensing and detection performed by these devices to detect exposure to RF and magnetic fields.

BACKGROUND

A wide variety of implantable medical systems that deliver a therapy or monitor a physiologic condition of a patient have been clinically implanted or proposed for clinical implantation in patients. An example implantable medical system may include an implantable medical lead connected to an implantable medical device (IMD). For example, implantable leads are commonly connected to implantable pacemakers, defibrillators, cardioverters, or the like, to form an implantable cardiac system that provides electrical stimulation to the heart or sensing of electrical activity of the heart. The electrical stimulation pulses can be delivered to the heart and the sensed electrical signals can be sensed by electrodes disposed on the leads, e.g., typically near distal ends of the leads. Implantable leads are also used in neurological devices, muscular stimulation therapy, gastric system stimulators and other implantable medical devices (IMDs).

Patients that have implantable medical systems may benefit, or even require, various medical imaging procedures to obtain images of internal structures of the patient. One common medical imaging procedure is magnetic resonance imaging (MRI). MRI procedures may generate higher resolution and/or better contrast images (particularly of soft tissues) than other medical imaging techniques. MRI procedures also generate these images without delivering ionizing radiation to the body of the patient, and, as a result, MRI procedures may be repeated without exposing the patient to such radiation.

During an MRI procedure, the patient or a particular part of the patient's body is positioned within an MRI device. The MRI device generates a variety of magnetic and electromagnetic fields to obtain the images of the patient, including a static magnetic field, gradient magnetic fields, and radio frequency (RF) fields. The static magnetic field may be generated by a primary magnet within the MRI device and may be present prior to initiation of the MRI procedure. The gradient magnetic fields may be generated by electromagnets of the MRI device and may be present during the MRI procedure. The magnetic and RF fields may be generated by transmitting/receiving coils of the MRI device and may also be present during the MRI procedure.

If the patient undergoing the MRI procedure has an implantable medical system, the various fields produced by the MRI device may have an effect on the operation of the medical leads and/or the IMD to which the leads are coupled. For example, the gradient magnetic fields or the RF fields generated during the MRI procedure may induce energy on the implantable leads (e.g., in the form of a current). The current induced on the implantable leads may cause the IMD to sense a cardiac signal when one is not present, a phenomenon referred to as oversensing, or to not sense a cardiac signal when one is present, a phenomena referred to as undersensing. Oversensing and undersensing may result in the IMD delivering therapy when it is not desired or withholding therapy when it is desired. A need exists for improvements to IMDs that reduce or eliminate the impact of magnetic fields to the IMD operation.

SUMMARY

In accordance with an aspect of the invention, an apparatus is provided for detecting exposure of an implantable medical device to magnetic fields. The apparatus includes a three-axis magnetic sensor having a plurality of sensor integrated circuits (ICs) that are aligned in at least three axes, i.e., the X, Y, and Z axis.

In an embodiment, the three sensor ICs may be coupled to a processor adapted to receive detection signals generated by one or more of the three sensor ICs in response to exposure to a magnetic field force. The processor may evaluate the strength of the magnetic field force and perform a predetermined action in response to the strength of the detected magnetic field.

In an aspect of the invention, a method is provided for construction of a magnetic sensor. In the method, a substrate is provided with an array of panels with each of the panels having a plurality of subpanels. An IC is electrically coupled to each of the subpanels and stabilized to the substrate with an underfill material. The subpanels corresponding to each panel are excised from the substrate and folded to orient the ICs in three independent axis. For example, the three subpanels may be folded to orient the ICs in mutually orthogonal axis.

In another aspect of the invention, a method is provided for forming a magnetic sensor. In one embodiment, a method includes mounting three single-axis magnetic sensor integrated circuits (ICs) to a substrate. The ICs are encapsulated to the substrate with a polymer mold compound. The substrate is excised around each of the sensor ICs to form panels that are folded to align the three single-axis sensors in the X, Y, and Z axis.

In another embodiment, a method includes mounting three single-axis magnetic sensor integrated circuits (ICs) to a substrate. The substrate is excised around each of the sensor ICs and folded to orient the ICs in three independent axis. For example, the folding of the substrate may orient the sensor ICs in a mutually orthogonal three-dimensional orientation. The folded substrate is encapsulated with a polymer mold compound.

BRIEF DESCRIPTION OF THE DRAWINGS

The invention may be understood by reference to the following description taken in conjunction with the accompanying drawings, in which like reference numerals identify like elements, and in which.

Figure 1:
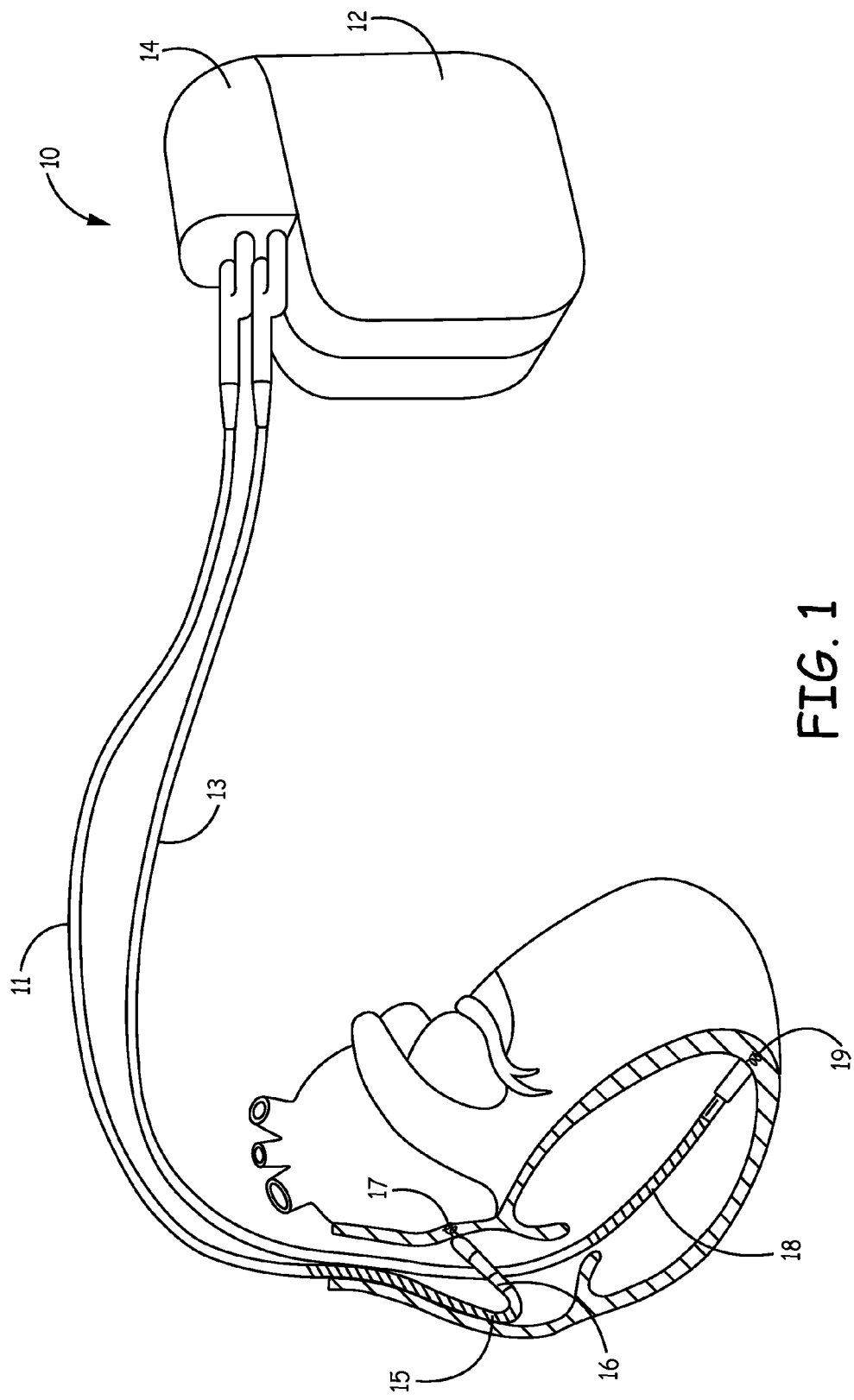
FIG. 1 is a schematic of an exemplary medical system according to some embodiments of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention.

Early telemetry communication schemes in implantable medical devices (IMD) included a single axis Hall sensor for communication between a programmer and the IMD. The single axis hall sensor has been utilized to initiate communication between the IMD and an external programmer In such communication schemes, the magnetic field can be aligned with the geometry of the implanted IMD, i.e., both the implant orientation of the implanted IMD is known as is the magnetic field of the programmer magnet. Apart from the telemetry communication schemes, detecting exposure of IMDs to magnetic fields is useful in other contexts. In this disclosure, all varieties of magnetic and electromagnetic fields, including static magnetic fields, gradient magnetic fields, and radio frequency (RF) fields, will be referred to interchangeably, and unless specified, it being understood that reference to one does not exclude any other known types of such fields. However, the orientation of the magnetic field is not always known in such contexts and therefore, the single axis magnetic sensors utilized for communications may not detect the presence of the magnetic field force. This may be problematic for continued operation of the IMD to prevent interruption of IMD operations in the presence of a magnetic force.

FIG. 1 is a schematic of an exemplary medical system according to some embodiments of the present invention. The system includes IMD 10 to which a right atrial medical electrical lead 11 and a right ventricular medical electrical lead 13 are operatively coupled via a connector module 14. Lead 11 is shown including a defibrillation electrode 15, a first pace/sense electrode 16 and a second pace/sense electrode 17, which is contacting tissue of a right atrial appendage. Lead 13 is shown including a defibrillation electrode 18 and a pace/sense electrode 19 fixed to tissue in a right ventricular apex. According to the illustrated embodiment, IMD 10 includes a can or housing 12, which serves as another defibrillation electrode to act in concert with electrodes 15 and 18. The system shown in FIG. 1, well known to those skilled in the art, is configured for cardiac pacing, sensing and defibrillation. According to embodiments of the present invention, the system further includes a capacity to detect a magnetic field and respond to the detected field, such that electrical signals induced in either one or both of leads 11, 13, by the gradient magnetic field do not adversely affect operation of the IMD.

Magnetic fields like those produced by magnetic resonance imaging (MRI) devices may disrupt the normal operation of the IMD 10. For example, the RF and magnetic fields may generate currents in the IMD 10 that may cause its components to overheat, potentially leading to tissue damage. The magnetic fields may also cause the IMD 10 to deliver improper therapies. Hereinafter, magnetic fields that may disrupt the normal operation of the IMD 10, like those that may be found in MRI devices, will be referred to as "magnetic field activity." Although not so limited, magnetic field activity may include a static magnetic field ranging from 0.2 Tesla to 3 Tesla, a pulsed gradient magnetic field, and a pulsed radio-frequency magnetic field. However, it should be noted that this term is not limited to magnetic fields found in MRI devices, and may refer to magnetic fields that may be found in any one of a variety of environments.

Figure 2:
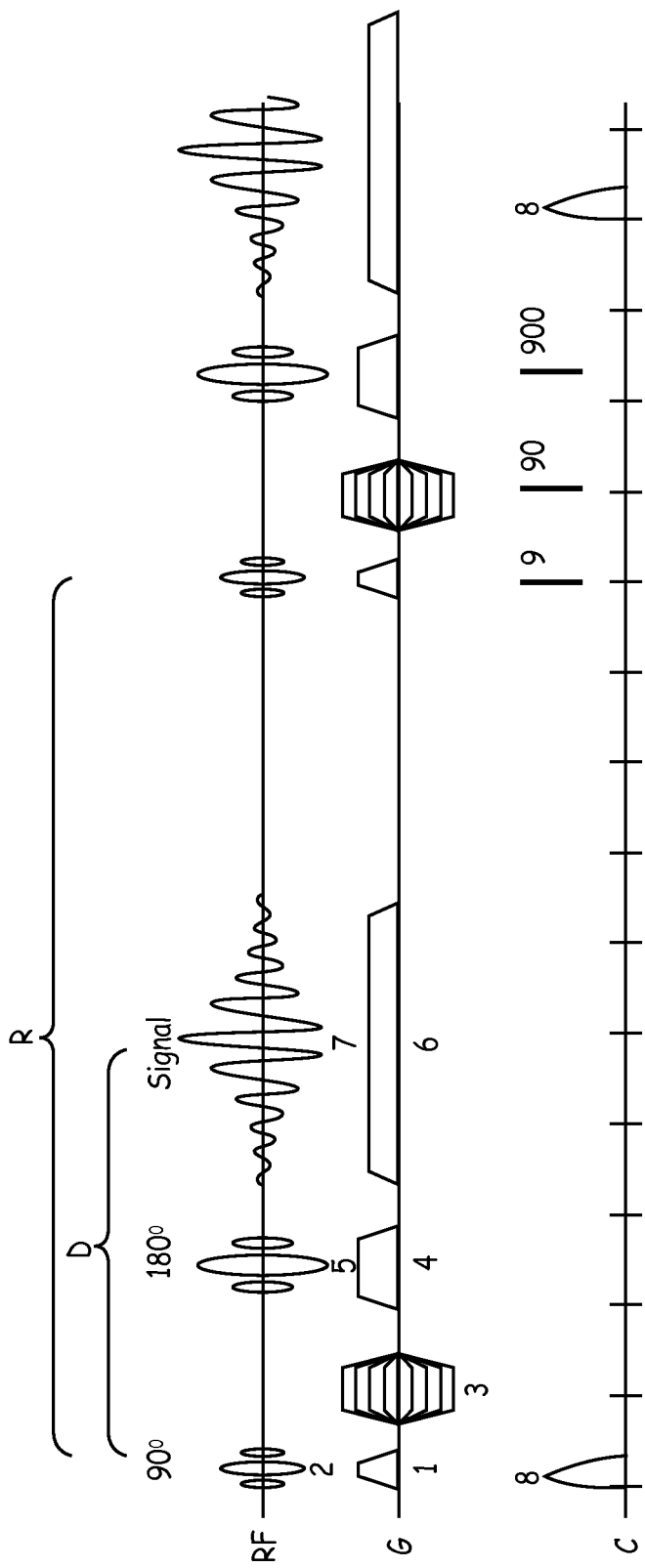
FIG. 2 is a collection of exemplary plots representing artifact-inducing magnetic field activity and cardiac electrical activity.

FIG. 2 is a collection of exemplary plots representing artifact-inducing magnetic field activity and cardiac electrical activity. Those skilled in the art understand that, in order for RF pulses to produce a signal for MRI imaging, a magnetic field must be altered on a local level coinciding with a location at which the image is desired. Plots RF and G of FIG. 2 represent a sequence of MRI induced RF pulses and associated gradient magnetic fields, respectively; those skilled in the art will recognize slice select gradients 1 and 4 associated with a 90° RF pulse 2 and a 180° RF pulse 5, respectively, and a phase encoding gradient 3, for first phase encoding, and a read out gradient 6 activated while signal 7 is sampled. If a lead wire, for example one included in lead 13 of FIG. 1, is coincident with the location at which the image is being generated, the wire will pick up electrical artifacts generated by the gradient fields and RF pulses. Since a magnitude of a RF pulse artifact is typically greater than 3 volts whereas cardiac electrical activity is on the order of millivolts, the RF artifact can be erroneously detected as a cardiac event, i.e. ventricular depolarization, and can completely mask or 'drown out' signals of actual cardiac events.

In order to demonstrate interference of the magnetic field activity, FIG. 2 further shows, under the RF and G plots, a third plot C representing normal cardiac electrical activity in terms of ventricular depolarization, or R-waves 8, for example sensed by electrodes 19 and 18 of FIG. 1. A time scale for each plot of FIG. 2 is 50 milliseconds per hash mark shown along plot C, but plots RF and G may shift with respect to the electrical activity shown on plot C depending on when the magnetic field activity is initiated within the cardiac cycle, represented by the interval between R-waves 8. Those skilled in the art will appreciate that a timing of RF and G events can vary. For example, each sequence of magnetic gradient fields and RF pulses may have a duration D between approximately 5 and 250 milliseconds and a time between sequences R may be between approximately 100 and 3,000 milliseconds; furthermore, a normal interval between R-waves 8, or an R-R interval, may be between approximately 600 and 1200 milliseconds. FIG. 2 illustrates D at approximately 250 milliseconds, R at approximately 500 milliseconds, and the R-R interval, along plot C, at approximately 700 milliseconds. With reference to FIG. 2, if plot C represents paced cardiac activity, for example, for a bradycardia patient, the RF pulse coincident with a marker 9, shown along plot C, may be detected as an intrinsic R-wave causing a device, e.g., IMD 10, to withhold the second pacing pulse shown at the far right hand side of plot C. It will be appreciated that if the plots RF and G shift in time with respect to the plot C, the RF pulse will coincide with either markers 90 or 900 to be detected as a cardiac event. Thus, it can be seen that RF pulse timing coinciding with normal to slower rhythms, i.e. in the range of 600 to 1200 milliseconds, may cause IMD 10 to withhold pacing therapy when it may be needed. Alternately, RF pulse timing in the range of 100 to 600 milliseconds coincides with dangerously fast rhythms, for example ventricular tachyarrhythmia (VT) and ventricular fibrillation (VF), and can cause IMD 10 to falsely detect VT or VF and thus deliver unneeded pacing and/or high voltage therapy delivery.

Figure 3A:
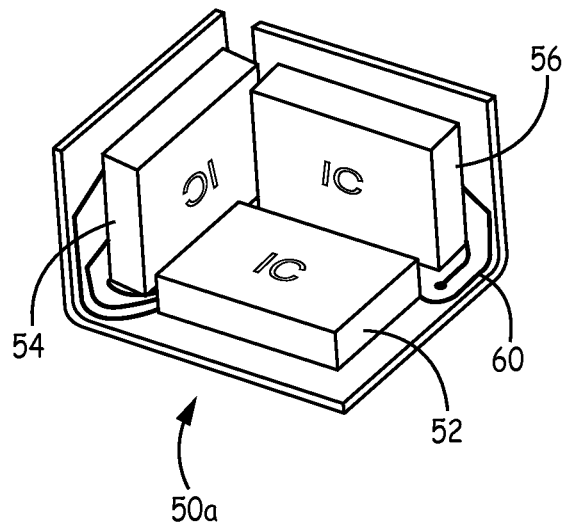
FIG. 3A is a perspective view of an embodiment of a magnetic sensor, which can detect magnetic field activity along any one or more of an x, y, or z axis, depending upon the orientation of the field.
Figure 3B:
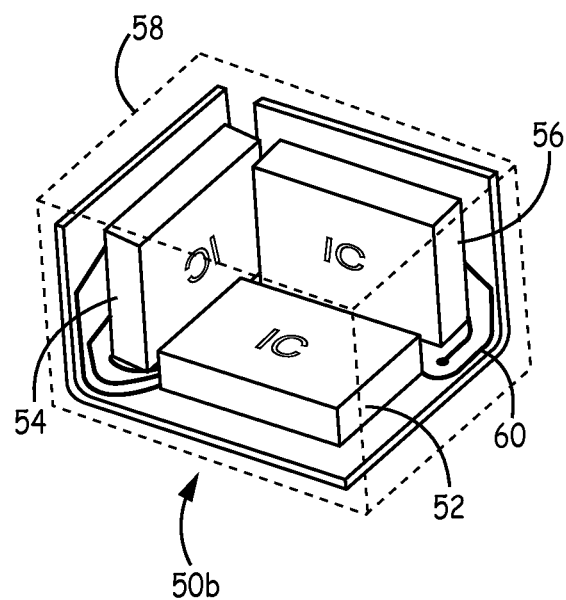
FIG. 3B is a perspective view of an alternative embodiment of a magnetic sensor, which can detect magnetic field activity along any one or more of an x, y, or z axis, depending upon the orientation of the field.

FIGS. 3A and 3B are perspective views of alternative embodiments of a magnetic sensors 50a, 50b, respectively. Magnetic sensors 50a, 50b (collectively "sensor 50") can detect magnetic field activity along any one or more of an x, y, or z axis, depending upon the orientation of the field. The magnetic sensor 50 includes three sensor integrated circuits (ICs) 52, 54, 56 mounted on a substrate 60. Each of the ICs 52, 54, 56 comprises a single-axis field transducer. In one embodiment, each of the ICs 52, 54, 56 comprises a solid state transducer, such as a Hall-effect or a magnetoresistive transducer.

The ICs 52, 54, 56 are configured in three independent axis. In the illustrative embodiment, the ICs 52, 54, and 56 are oriented in mutually orthogonal relationship such that each IC is adapted to detect magnetic field components in one of the x, y, or z axis. For example, if the sensor 50 is oriented in the depiction of FIG. 3A or 3B, IC 52 will detect magnetic fields aligned perpendicular to the X-axis plane, IC 54 will detect magnetic fields aligned perpendicular to the Y-axis plane, and IC 56 will detect magnetic fields aligned perpendicular to the Z-axis plane. Each of the ICs 52, 54, 56 in turn generates a detection signal approximately proportional to the strength of the detected magnetic field. Such detection signals may, in one embodiment, comprise a voltage or current, related to the strength of the component of the magnetic field directed approximately perpendicular to the given plane.

Magnetic sensor 50a shown in FIG. 3A differs from the magnetic sensor 50b in FIG. 3B in that sensor 50b includes an encapsulating layer 58 that encapsulates the constituent components. The assembly techniques that yield the alternative embodiments will be discussed below in conjunction with FIGS. 4A to 4E.

Sensor 50 in accordance with one embodiment of the invention is used in conjunction with an implantable medical device, such as IMD 10. Such a sensor 50 may physically be incorporated into the IMD 10 circuitry (e.g., FIG. 5) for detecting magnetic field components along one or more independent directions, including mutually orthogonal directions.

Figure 4A:
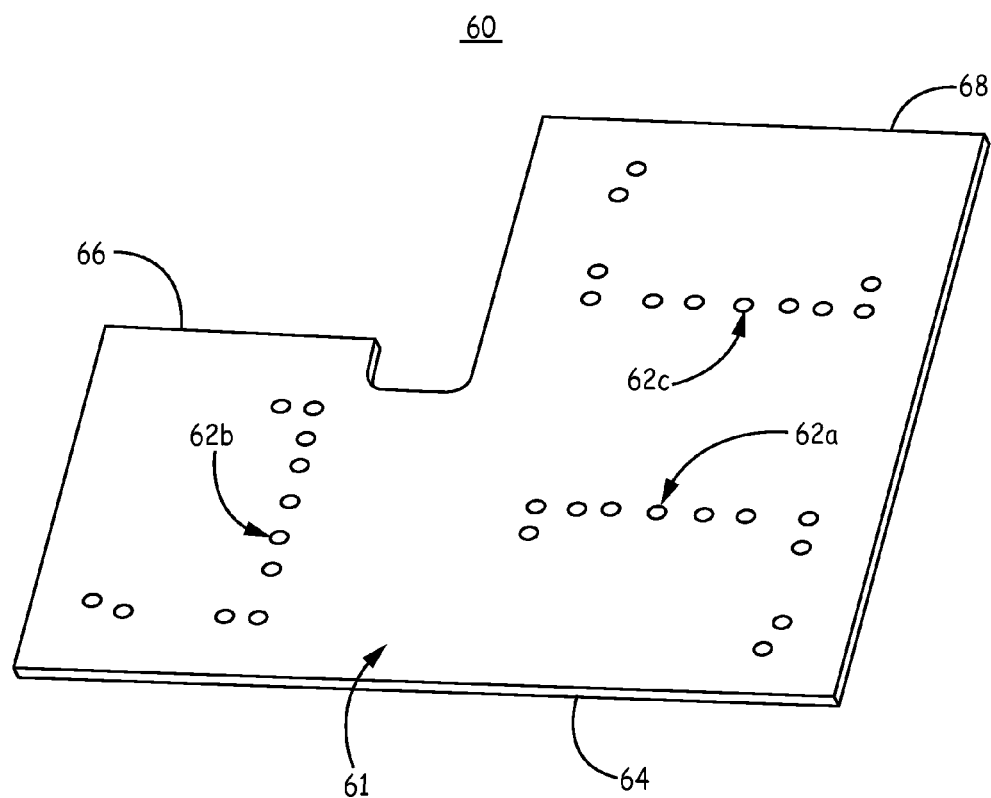
FIGS. 4A, 4B, 4C, and 4D illustrate an exemplary process of construction of the magnetic sensor.
Figure 4B:
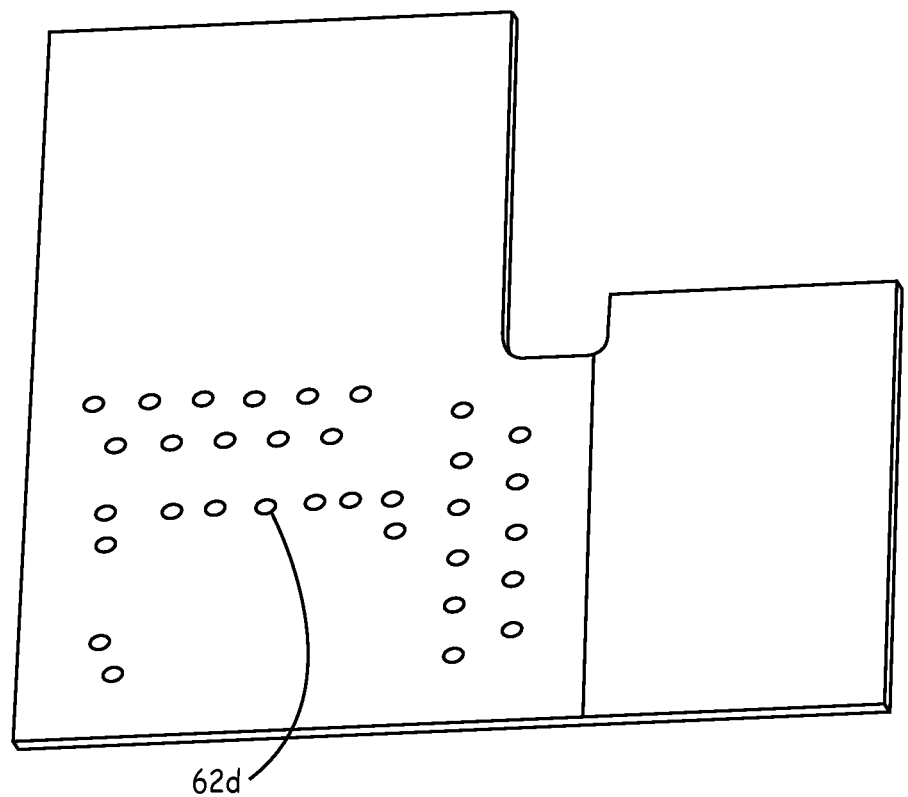
Figure 4C:
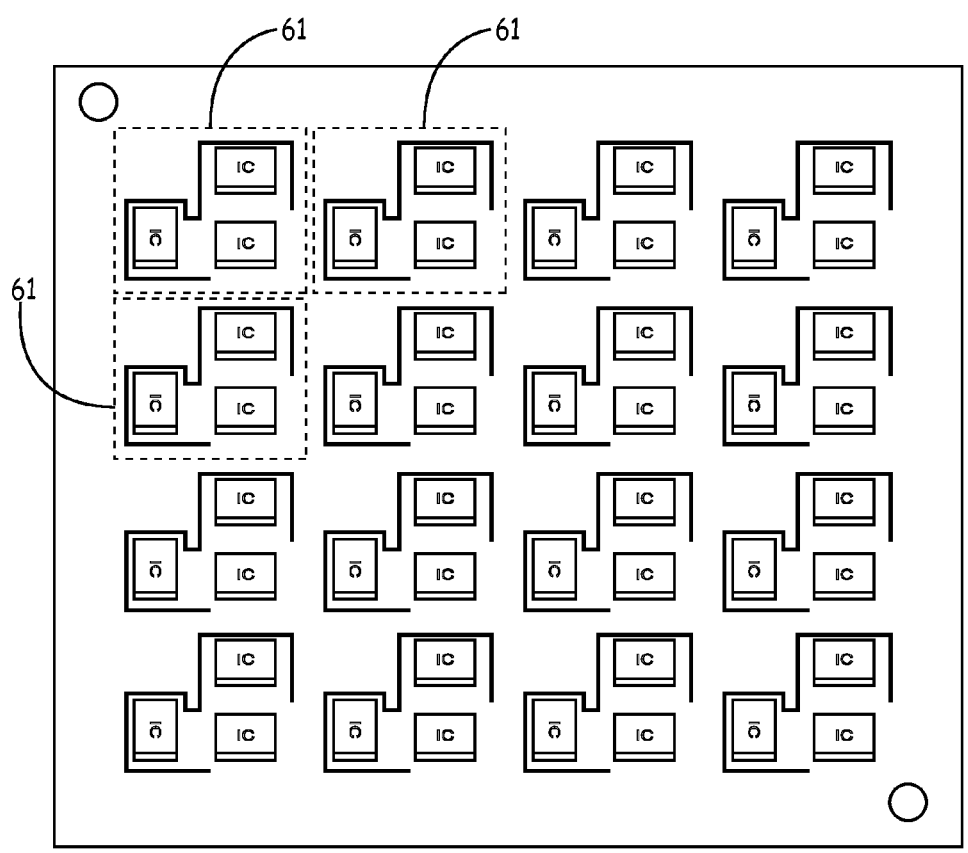

FIGS. 4A to 4E illustrate exemplary processes of construction of sensor 50. In one embodiment, the construction process is initiated by providing substrate 60 comprising an array of portions 61. In one illustrative embodiment, substrate 60 comprises a malleable or flexible circuit board that is initially a straight board but is subsequently bendable and/or foldable into a three-dimensional geometry. As illustrated in FIG. 4A, the substrate 60 includes a conductive trace pattern on the top side for mounting the integrated circuits (ICs) of the magnetic sensor 50. Turning to FIG. 4B, the back side of the substrate 60 is shown including exposed pads 62d for coupling the array of magnetic sensors 50 to a circuit of the IMD 10. The pads 62d are electrically coupled to the conductive trace patterns 62a, 62b, 62c and therefore couple the ICs 52, 54, 56 to the IMD 10 circuitry. In FIG. 4C, substrate 60 is shown having multiple portions 61 onto which a plurality of magnetic sensors 50 may be mounted. In such an example, the substrate 60 will typically be sized to accommodate a plurality of magnetic sensors 50 for large scale manufacturing, and therefore multiple duplicate circuit trace patterns may be formed on multiple portions 61 of any given one of such substrates 60. Each of the portions 61 on substrate 60 defines a panel that includes a plurality of subpanels onto which the ICs of the magnetic sensor 50 are mounted. In an embodiment, each magnetic sensor 50 may be formed within one of the panels defined by one of the portions 61 that includes three subpanels. The three subpanels define a base panel 64 and first and second side panels 66, 68 onto which ICs 52, 54, 56 are bonded. The layout of the trace patterns on the three subpanels is performed such that a first trace pattern e.g., 62a is aligned in a parallel orientation with a second trace pattern e.g., 62c and a third trace pattern e.g., 62b is aligned perpendicular to the first trace pattern e.g., 62a. In the embodiment, electrical connections between each of the three ICs 52, 54, and 56 is made to the respective subpanel through a reflow or other soldering process. For example, the ICs 52, 54, 56 may be provided in a conventional BGA package that includes external terminals that can be reflowed to attach the IC package to terminals on the respective substrate subpanels 64, 66, and 68. In another embodiment, the ICs may be provided as flip chip components, without a package, for coupling to the substrate subpanels 64, 66, and 68. The traces may all be terminated at a common location, for example on the base panel 64 for electrical connectivity to other circuits of IMD 10.

Subsequent to the electrical terminal attachment of the ICs 52, 54, 56 to the respective panel portions 61 on substrate 60, an underfill is performed whereby the gap between the ICs and the substrate 60 is filled with an encapsulant in one embodiment. The underfill reinforces the interconnect material and absorbs some of the stress of the encapsulation process. Another function of the underfill is to reinforce the ICs against mechanical shock such as impact or vibration. This is especially important for preserving the integrity of the component in the subsequent process tasks. The underfill material may include an epoxy that may be electrically insulative.

Figure 4D:
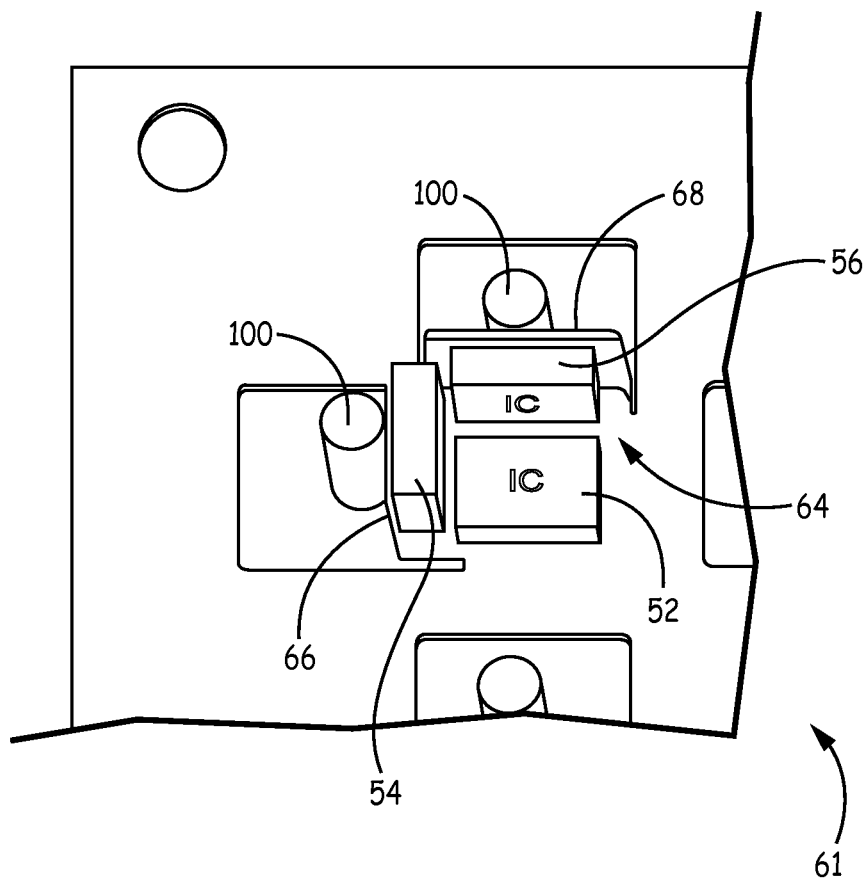

FIG. 4D illustrates a first embodiment showing the subpanels of one exemplary portion 61 having the side subpanels 66, 68 excised and folded following the underfill process. The subpanels 66 and 68 are folded such that the ICs 52, 54 and 56 are oriented in independent axis, such as in a mutual orthogonal relationship. That is, IC 52 is aligned perpendicular to the X axis, IC 54 is aligned with the Y axis and IC 56 is aligned with the Z axis. The excise cuts may be made utilizing any suitable technique. For example, a laser beam may be utilized to perform the excising of the side panels. The subpanels may further be permanently positioned in the folded configuration by applying an adhesive. The resulting configuration of this embodiment is as depicted in the embodiment illustrated in FIG. 3A.

Turning to FIG. 4E, an alternative method for forming the sensor 50 is illustrated. The alternative construction method results in formation of a molded sensor 50, such as that illustrated in FIG. 3B. Following the attachment of the ICs 52, 54, 56 to the respective portions 61 on substrate 60, a mold base having pins 100 is utilized to temporarily affix the folded side panels 66, 68 in the folded configuration. A molding material is dispensed over each of the panels 64, 66, and 68 to encapsulate the ICs 52, 54, 56 a common molded encapsulation. The molding material may be any suitable encapsulation epoxy such as epoxy. The substrate 60 may be molded including distinct three-sensor IC blocks that form the three panels 64, 66, 68. Alternatively, the entire substrate 60 may be molded and then sawn to create the three-sensor IC blocks that form the three panels 64, 66, 68.

In an alternative embodiment, the task of underfilling the gap between the substrate and ICs may be performed in conjunction with the molding task. In this process, the molding material is initially dispensed to fill the gap. Next, the material is dispensed over the ICs 52, 54, and 56 to form individually encapsulated sensor blocks, each including one of the ICs 52, 54, 56. The individually encapsulated sensor blocks are then folded into a pre-defined configuration such as that shown in the embodiment of FIG. 3B.

As illustrated in FIG. 4E, each magnetic sensor 50 is formed having ICs 52, 54, 56 oriented in a mutually orthogonal relationship for detection of magnetic fields that are perpendicular to the X, Y, or Z axis, respectively. In embodiments in which the substrate 60 is provided for forming a plurality of magnetic sensors 50, the substrate is diced to separate each individual sensor 50.

One challenge in forming the sensor 50 including molding the sensor in the folded configuration, as discussed above where the side panels are folded prior to dispensing the encapsulant material, is in preventing the leakage of the material to the back side of the substrate. Dispensing the encapsulant material with the panels folded may result in the material flowing onto the back side to cover some or all of a portion of the pads that interconnect the sensor 50 to the IMD circuitry. Therefore, sufficient pressure needs to be maintained between the mold base and the substrate to seal the perimeter of the base panel 64 and therefore prevent the molding compound from seeping onto the back side and covering the pads.

In yet another embodiment, the panels 64, 66, 68 may be encapsulated prior to the task of folding. In that process, the molding material is dispensed over the panels while the panels of the substrate 60 are disposed in a flat orientation. Similar to the embodiment discussed above, the underfill may be dispensed in a separate process step prior to the encapsulation, or in conjunction with the encapsulation step. The encapsulated side panels 66, 68 may subsequently be excised to enable folding of the panels in an orthogonal three-dimensional orientation.

In some embodiments, an adhesive may be applied to the panels of the folded package of the sensor 50 to permanently affix the panels 64, 66, 68 in a configuration that has three independent axis. Alternative embodiments may utilize any other suitable bonding techniques that may be utilized for the mold material.

Figure 5:
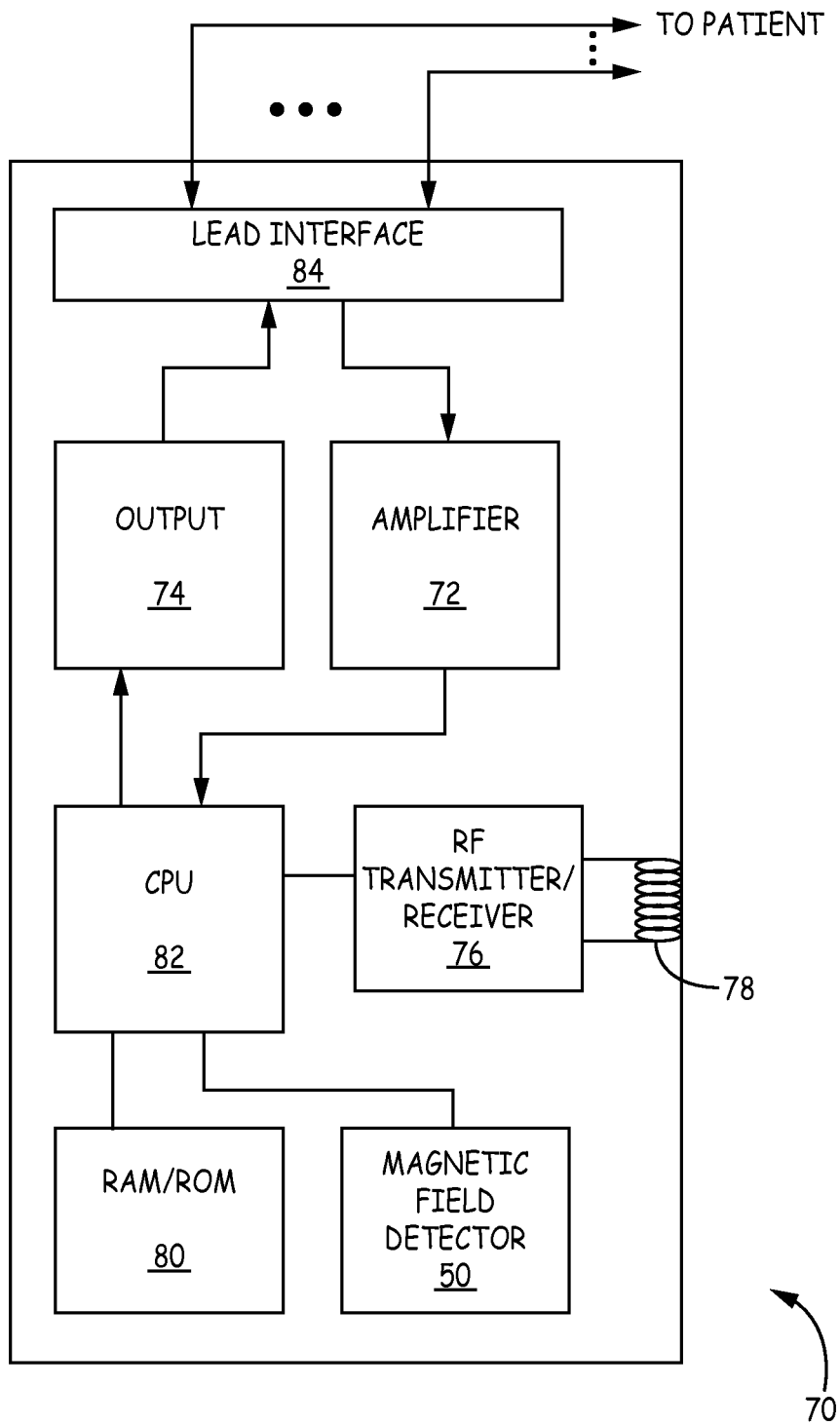
FIG. 5 is a functional block diagram corresponding to the system of FIG. 1 illustrating an exemplary microprocessor controlled system architecture into which the sensor is integrated.

FIG. 5 is a functional block diagram corresponding to the system of FIG. 1, which illustrates an exemplary microprocessor controlled system architecture, known to those skilled in the art, into which sensor 50 is integrated. It should be noted that other embodiments of the present invention may be practiced with other types of system architecture known to those skilled in the art, such as those employing dedicated digital circuitry.

Although not so limited, the processor unit 70 may include such components as an amplifier 72, an output 74, a transmitter/receiver 76 coupled to an antenna 78, a random-access memory and read-only memory (RAM/ROM) unit 80, a central processing unit (CPU) 82, and a lead interface 84, which functions, in a multiplexer-like manner, to establish necessary connections between the leads 11 and 13 and individual electrical components of the processor unit 70. However, it will be appreciated that additional components, such as clocks and I/O devices which are not shown in FIG. 5, may be included in the processing unit 70 without departing from the spirit or scope of the instant invention.

According to one embodiment, the CPU 82 may be adapted to receive physiological data over the leads. The data transmitted by the leads may take the form of electric currents or voltages that may be amplified by the amplifier 62 before being transmitted to the CPU 82. In one embodiment, the CPU 82, acting under control of software stored in the RAM/ROM unit 80, may collect and store the physiological data in the RAM/ROM unit 80. The CPU 82 may use the physiological data to determine when it may be desirable to provide a therapy to the patient (not shown) through the output 74. For example, data indicating the timing of recent heartbeats may be used to detect an arrhythmic heart beat, in which case the CPU 82 may direct the output 74 to provide an electric discharge that may be transmitted through the lead interface 84 to the heart via the leads.

Occasionally, it may be desirable to non-invasively program the CPU 82. For example, a doctor may determine that a smaller or larger electrical discharge may provide a more effective therapy to treat heart arrhythmia in the patient. In one embodiment, the transmitter/receiver 76 may be adapted to receive radio-frequency (RF) signals through the antenna 78. The RF signals may be used to non-invasively program the CPU 82. However, because the transmitter/receiver 76 may not be used frequently, the power consumed by the receiver may be limited by turning off the receiver when it is not receiving signals. According to one embodiment, the power supplied to the receiver may be restored to enable non-invasive programming by applying a probe field to close a switch (not shown) in the receiver.

The amplifier 72 may also be exposed to magnetic fields that may disrupt its operation. For example, in one embodiment, magnetic fields such as the pulsed radio-frequency magnetic field may create electric currents that may that may be transmitted to the amplifier 72. This may cause the CPU 82 to misinterpret the information received from the amplifier 72, and cause the output to deliver inappropriate electrical stimuli to the patient through the leads, which may damage tissue in the patient. Thus, in one embodiment, the processor unit 70 may further comprise magnetic activity sensor 50, which may be adapted to detect both the probe fields, such as those used to turn on the transmitter/receiver 76, and the static magnetic field that may indicate the presence of disruptive magnetic field activity such as the pulsed gradient magnetic field and the pulsed radio-frequency magnetic field. In the event that the magnetic activity sensor 50 detects the presence of the static magnetic field, the magnetic activity sensor 50 may be adapted to instruct the CPU 82 to enter into the safe mode of operation. In an embodiment, additional circuitry (not shown) may be included in the processor unit 70 to facilitate the transmission of the magnetic field detection signal to the CPU 82. For example, a semiconductor OR gate may be provided to electrically couple signals from each of the three hall sensors of the magnetic activity sensor 50 to the CPU 82.

Although magnetic fields like those produced by MRI devices may be disruptive to the operation of the IMD 10, it is important to note that not all magnetic fields that may be applied to the IMD 10 are disruptive. For example, a small magnetic field may be applied to the IMD 10 as a step in a method of non-invasively programming the IMD 10. However, it will be appreciated that the aforementioned term will not be limited to magnetic fields used for programming the IMD 10, but may include magnetic fields that may be found in a variety of environments.

To better distinguish between non-disruptive probe fields and potentially disruptive magnetic field activity, the IMD 10 may be adapted to detect static magnetic fields above a certain magnetic field strength threshold, such as those that may generally be found in or near an MRI device. The aforementioned three-dimensional magnetic activity sensor 50 may enable the IMD 10 to reliably detect the magnetic field that may indicate the presence of disruptive magnetic field activity. The IMD 10 may further include one or more devices adapted to use the signals produced by the magnetic activity sensor to notify the processor that it may be desirable to enter the safe mode. By instructing the IMD 10 to enter the safe mode when the IMD 10 may be exposed to magnetic fields like those found in MRI devices, the magnetic activity sensor may allow the IMD 10 to reduce tissue damage to the patient, as well as reduce the probability of administering inappropriate therapies.

Figure 6:
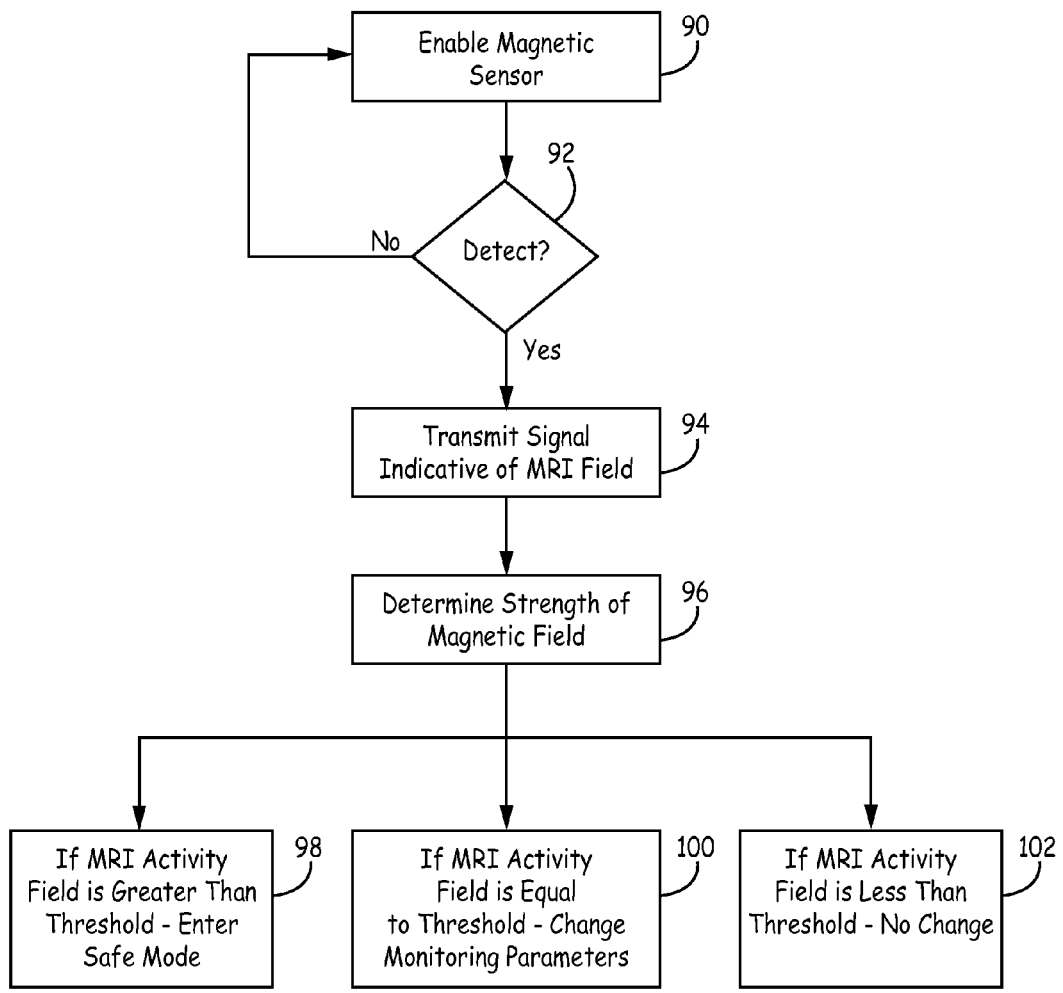
FIG. 6 is a flow diagram illustrates one method for detection of exposure of an implantable medical to a magnetic field.

Turning now to FIG. 6, a flow diagram illustrates one method for detection of exposure of an implantable medical to magnetic field activity. In accordance with FIG. 6, the three-axis magnetic activity sensor 50 detects magnetic field activity in any of the X, Y, or Z axis. The magnetic activity sensor 50 may be continuously or periodically enabled for detection of magnetic field activity (90). The outputs of each of the sensor ICs 52, 54, 56 are monitored to detect the presence of magnetic fields directed approximately perpendicular to the X axis IC 52, Y axis IC 54, or Z axis IC 56 (92). In response to detecting a magnetic field, the ICs 52, 54, 56 generate a detection signal, e.g., current or voltage, which is proportional to the magnetic field strength. The detection signal indicative of the magnetic field strength is transmitted to the CPU 82 (94). The CPU 82 may process the detection signal to, among other things, determine the strength of the magnetic field (96).

If the magnitude of the magnetic field exceeds a threshold value for a static MRI magnetic field, e.g. 1700 Gauss, the CPU 72 may change an operating mode of the IMD 10 (98). For example, a sensing and/or therapy delivery function of the IMD 10 may be changed to a predetermined mode that is deemed safe or less susceptible to magnetic fields. For example, the safe mode may comprise measures adapted to reduce the high electric currents that may be generated in the IMD 10 by magnetic fields and that may erroneously stimulate tissue, as well as causing sensors in the IMD 10 to oversense and/or undersense conditions in the patient's body in such a way that may lead to the IMD 10 providing improper therapies. Although not so limited, the safe mode may comprise such tasks as reducing power to components in the IMD 10 and/or turning off amplifiers that may monitor signals from leads. For patients with low or no intrinsic heart rhythm, the safe mode may provide pacing therapy at a predetermined lower rate. In another example, the magnetic field monitoring parameters may be changed to, for instance, increase the monitoring frequency or to revert to continuous monitoring. If the magnitude of the magnetic field is equal to a threshold value for a static MRI magnetic field, e.g. 1700

Gauss, the CPU 72 may continue with the then current operating mode and issue an instruction to the sensor 50 to increase the monitoring frequency of the magnetic field detection (100). If, however, the magnitude of the magnetic field is less than a threshold value for a static MRI magnetic field, e.g. 1700 Gauss, the CPU 72 makes no changes to the IMD 10 operating mode and the magnetic field detection continues in accordance with the currently programmed parameters (102).

In some embodiments, the processing performed by CPU 72 further includes discriminating the orientation of the magnetic field. For example, the CPU 72 may determine whether the magnetic field activity is predominantly along the X axis, the Y axis, or the Z axis.

The magnetic activity sensor 50 such as that described above may substantially reduce the probability that magnetic fields like those that may be found in MRI devices may cause the IMD 10 to malfunction and potentially harm the patient. In response to detection of the exposure to magnetic fields like those that may be encountered in an MRI device, the IMD 10 may, in one embodiment, enter a safe mode that may substantially reduce the chance that the IMD 10 may malfunction. The IMD 10 may leave the safe mode once the magnetic fields are no longer detected. For example, when the patient leaves the MRI room, the magnetic activity sensor 50 may instruct the CPU 72 to turn off the safe mode and revert to normal operation. The IMD 10 may also provide diagnostic information with a time stamp to indicate when the presence of a high magnetic field was detected. This diagnostic information may aid the health professional in determining if the MRI scan affected the sensing or stimulation thresholds, or if other environments the patient encountered in their daily life exposed them to a high magnetic field.

The above description is intended to be illustrative, and not restrictive. For example, the above-described examples (or one or more aspects thereof) may be used in combination with each other. Other embodiments can be used, such as by one of ordinary skill in the art upon reviewing the above description. In the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An implantable medical device, comprising:
   a multi-dimensional magnetic sensor including:
      a substrate having a plurality of panels, each panel being separable from the others of the panels;
      three hall sensors positioned on each of the plurality of panels, each of the panels having at least one subpanel that is foldable, wherein the folding of the at least one subpanel allows the hall sensors to be oriented along three independent axis.

2. The implantable medical device of claim 1, wherein the multi-dimensional magnetic sensor is configured to detect an exposure of the implantable medical device to a magnetic field in at least one of the three axis.

3. The implantable medical device of claim 2, wherein a mode of operation of the implantable medical device is adjustable in response to detection of a magnetic field.

4. The implantable medical device of claim 3, wherein the adjustment of the mode of operation is selected from a list including at least one of:
   a first operating mode when a magnitude of the magnetic field is below a specified first threshold;
   a second operating mode when the magnitude of the magnetic field exceeds or equals the specified first threshold over a specified first duration; or
   a third operating mode when the magnitude of the magnetic field further exceeds or equals a specified second threshold over a specified second duration.

5. The implantable medical device of claim 4, wherein:
   the first operating mode includes an ambulatory operating mode, the second operating mode includes a battery status test mode in which the implantable medical device is configured to provide an indication to a user corresponding to a battery status;
   and the third operating mode includes a magnetic resonance imaging (MRI) safe mode.

6. The implantable medical device of claim 2, wherein detecting the exposure of the implantable medical device to the magnetic field includes monitoring at least one of a current and a voltage provided by at least one of the three hall sensors.

7. The implantable medical device of claim 1, wherein the folding of the at least one subpanel orients the hall sensors along three mutually orthogonal axis.

8. The implantable medical device of claim 1, further comprising an electrical interface connector disposed on a third subpanel including terminals for coupling the three hall sensors to a processor.

9. The implantable medical device of claim 1, further comprising electrical traces formed in each of the subpanels and coupling the three hall sensors to an electrical interface connector.

10. The implantable medical device of claim 1, further comprising circuitry to combine the output of each of the three hall sensors to obtain an indicator of a magnetic field, wherein the circuitry includes a semiconductor OR gate electrically coupled to each of the three hall sensors.

11. A method for forming a magnetic sensor package, comprising:
providing a substrate having a first surface configured for mounting a plurality of hall sensors and a second surface having pads for electrical coupling to an implantable medical device circuit hybrid;
electrically coupling the plurality of hall sensors to the substrate;
fixating each of the plurality of hall sensors onto the substrate;
excising a panel of the substrate including at least three of the plurality of hall sensors, wherein the panel includes at least three subpanels; and
folding one of the at least three subpanels to orient the at least three hall sensors along three independent axis.

12. The method of claim 11, further comprising molding the at least three hall sensors of each panel in the folded configuration to permanently orient the three subpanels in a mutually orthogonal orientation.

13. The method of claim 12, wherein the molding is performed subsequent to excising the subpanel and folding of two of the at least three subpanels.

14. The method of claim 13, further comprising placing the base substrate onto a mold fixture prior to performing the molding.

15. The method of claim 11, further comprising reflowing each of the plurality of hall sensors onto the base substrate.

16. The method of claim 15, wherein fixating each of the plurality of hall sensors comprises underfilling each of the plurality of hall sensors subsequent to the reflow.

17. The method of claim 11, further comprising molding the at least three hall sensors of each panel prior to folding the three subpanels.

18. The method of claim 17, wherein the fixating of each of the plurality of hall sensors comprises underfilling performed during the molding of the plurality of hall sensors utilizing the mold compound.

19. The method of claim 11, further comprising attaching the second surface of each panel to a hybrid substrate.

20. The method of claim 11, wherein the molding is performed prior to excising the panel and folding of at least one of the three subpanels.

* * * * *